United States Patent

Murashita et al.

[11] Patent Number: 6,135,959
[45] Date of Patent: Oct. 24, 2000

[54] ULTRASONIC DIAGNOSTIC APPARATUS

[75] Inventors: Masaru Murashita, Mitaka; Masunori Matuzaki, Ube, both of Japan

[73] Assignee: Aloka Co., Ltd., Tokyo, Japan

[21] Appl. No.: 09/246,592

[22] Filed: Feb. 8, 1999

[30] Foreign Application Priority Data

Feb. 9, 1998 [JP] Japan ................... 10-027323

[51] Int. Cl.$^7$ ................... A61B 8/00
[52] U.S. Cl. ................... 600/443; 600/450
[58] Field of Search ................... 600/440, 441, 600/443, 453–456, 450

[56] References Cited

U.S. PATENT DOCUMENTS

| | | |
|---|---|---|
| 5,322,067 | 6/1994 | Prater et al. |
| 5,465,721 | 11/1995 | Kishimoto et al. |
| 5,615,680 | 4/1997 | Sono ................... 600/454 X |
| 5,622,174 | 4/1997 | Yamazaki ................... 600/455 X |
| 5,669,387 | 9/1997 | Mine . |
| 5,800,356 | 9/1998 | Criton et al. ................... 600/455 X |
| 5,860,927 | 1/1999 | Sakaguchi et al. ................... 600/453 |
| 5,971,927 | 10/1999 | Mine ................... 600/455 |

Primary Examiner—Francis J. Jaworski
Attorney, Agent, or Firm—Cantor Colburn LLP

[57] ABSTRACT

An ultrasonic diagnostic apparatus which displays a two-dimensional sectional image of, for example, the left ventricle of the heart by sending and receiving ultrasonic waves. A reference point is set in the left ventricle, and an outline of the left ventricle is identified using this point. The left ventricle is radially divided from the reference point into plural division regions, e.g. four regions. The area of each division region is calculated at each point in time, and an area variation rate is computed from the ratio of the area and a reference area. The area variation rate for each division region is continuously displayed as a graph. On this graph, a part with dull motion (diseased part) can easily be identified.

11 Claims, 2 Drawing Sheets $$FAC = \frac{EDA - \Delta S}{EDA} \times 100$$

US 6,135,959

ULTRASONIC DIAGNOSTIC APPARATUS

BACKGROUND OF THE INVENTION

1. Field of the Invention

This invention relates to an ultrasonic diagnostic apparatus, and in particular to an apparatus which displays the movement of cardiac muscle in the heart as a graph.

2. Description of the Related Art

The Applicant, in JPA-09-253085 published by the Japanese Patent Office on Sep. 30, 1997, proposes an apparatus for graphically displaying muscle movement in the human heart using transmitted/received ultrasonic waves. This device displays a two-dimensional sectional image of the left ventricle of the heart. A reference point is set in the middle of the left ventricle manually or automatically, and plural reference lines are automatically set extending radially from the reference point. The surface of the cardiac muscle (specifically endocardium) is detected by performing a technique such as edge detection, etc., on the reference lines, and cardiac muscle movement on the reference lines is displayed as a graph.

The horizontal axis in the graph shows the azimuth (address of the reference line) seen from the reference point. The vertical axis in the graph shows the amount of movement of the cardiac muscle (distance from the reference point). The graph is updated in real time. If this graph which varies with time is observed continuously, it is easy to identify which azimuth surrounding the left ventricle, i.e. which cardiac muscle part, has a disease. Specifically, the movement of cardiac muscle parts which have a disease such as for example cardiac infarction is different from the movement of other, healthy parts. In general, the amount of the movement of the diseased part is small or abnormal.

However, in the aforesaid graphical display, the part in which there is an obstruction to motion cannot easily be determined merely by observing a graph at one point in time. That is, it is only by observing the graph continuously that it is possible to identify a diseased part.

It is therefore desirable to improve the graphical display to make diagnosis of cardiac disease easier. For example, it is preferable to evaluate each part of the cardiac muscle by observing only one graph.

SUMMARY OF THE INVENTION

It is therefore an object of this invention, which was conceived in view of the above problems, to display a new graph useful for diagnosis of internal organs (in particular, the heart) in an ultrasonic diagnostic apparatus.

It is a further object of this invention to provide a graph showing a time-dependent variation of the movement of each part of cardiac muscle in the heart.

To achieve the aforesaid objects, the ultrasonic diagnostic apparatus according to this invention comprises:

a transmitting/receiving wave unit for sending and receiving ultrasonic waves, and acquiring two-dimensional image data for each transmitted/received wave frame, an extracting unit for extracting an outline of a ventricle or an atrium of a heart based on said two-dimensional image data, a dividing unit for radially dividing an area inside said outline into plural division regions from a reference point set in said ventricle or atrium, an area computing unit for computing an area of each of said division regions for each of said transmitted/received wave frames, and a graph drawing unit for drawing a graph showing a time-dependent variation of the area or an area variation rate of each division region.

The above system extracts an outline of the ventricle or atrium of the heart based on two-dimensional image data. Various techniques can be used for the extraction, e.g. the technique described in JPA-09-253085. The area (region) inside the extracted outline is divided into plural sector-shaped regions. The number of parts into which the area is divided depends on the probability of disease and the function of the cardiac muscle. A graph showing the area or area variation rate of each division region is drawn, and this graph is displayed. One axis of the graph is the time axis, and the other axis represents the area or the area variation rate.

In this graph, a curve corresponding to a part where there is a cardiac infarction has a form different from other curves in the graph. As a result, it is easy to determine the presence or absence of disease and identify a diseased part.

Preferably, the area variation rate is computed using an electrocardiac signal from an electrocardiograph.

Further, the number of division regions inside the outline is preferably an integer in the range 4–6. When there are too many division regions, the graph becomes complex which interferes with the diagnosis. On the other hand, when there is an insufficient number of division regions, a graph which clearly indicates disease cannot be obtained and it becomes difficult to identify a diseased part. Considering these factors, the number of division regions is preferably 4, 5 or 6. Even with such a broad division, parts which are likely to be diseased can be identified to some extent, so a specific identification of diseased parts can easily be made.

DESCRIPTION OF THE PREFERRED EMBODIMENTS

Figure 1:
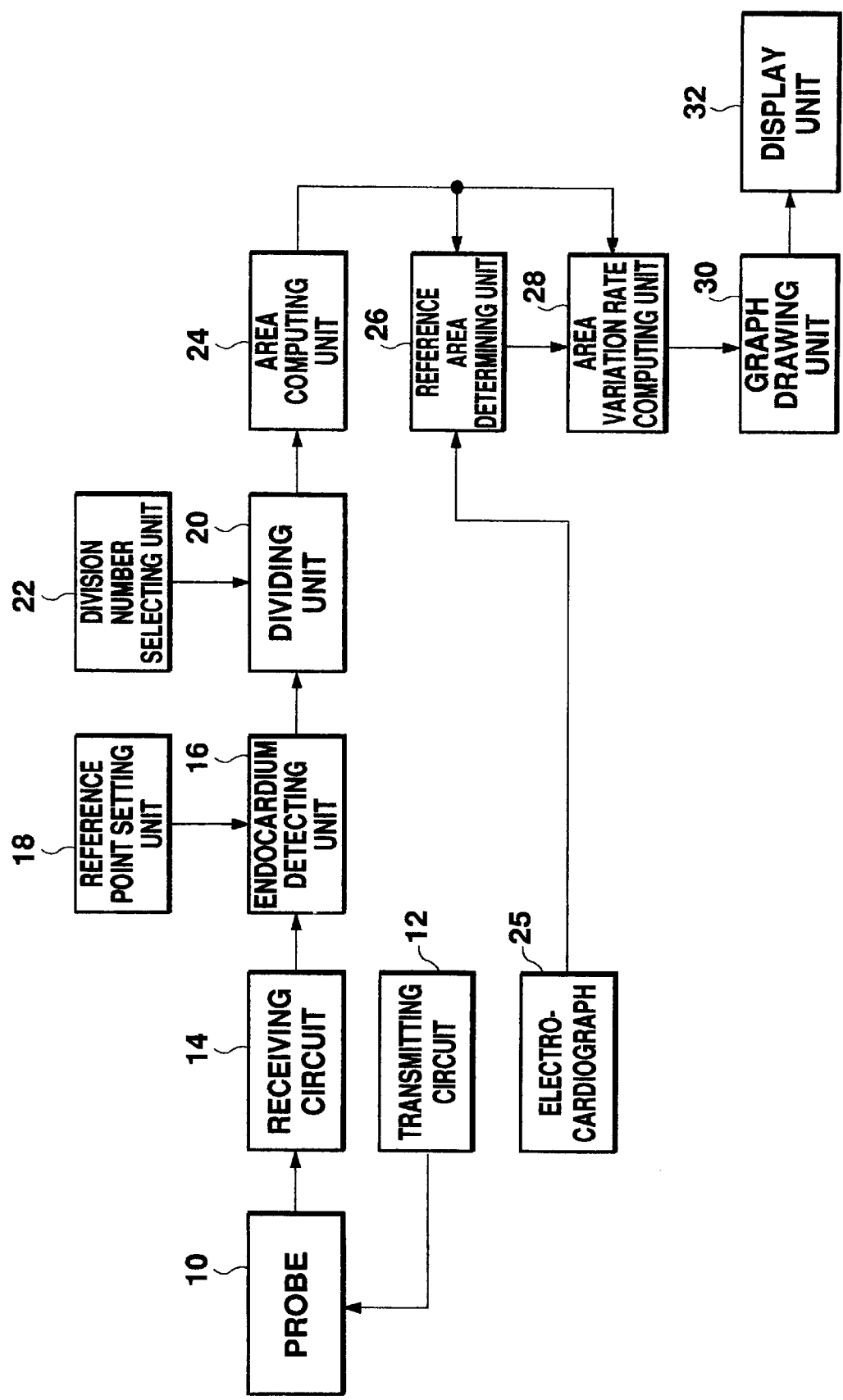
FIG. 1 is a block diagram showing one embodiment of the ultrasonic diagnostic apparatus relating to this invention.

A preferred embodiment of the ultrasonic diagnostic apparatus according to this invention is shown in FIG. 1. FIG. 1 is a block diagram showing its overall construction.

A probe 10 is a device used in contact with, for example, the surface of the chest. The probe 10 has a built-in ultrasonic transducer which transmits and receives ultrasonic waves. This ultrasonic transducer is an array transducer comprising, for example, plural elements. Electronic sector scanning or electronic linear scanning is performed relative to the array transducer according to the frame rate of transmitted/received waves. In this way, an ultrasonic wave beam scanning is performed, and a rectangular or sector-shaped two-dimensional data acquisition area is formed as a result.

The ultrasonic diagnostic apparatus shown in FIG. 1 has a mode which, in particular, measures the function of the heart. The construction of the apparatus relating essentially to this mode is shown in FIG. 1.

A signal is supplied to the probe 10 by a transmitting circuit 12. A received signal output from the probe 10 is output to a receiving circuit 14.

In the receiving circuit 14, amplification, detection and coordinate transformation are performed on the input signal. As a result, a two-dimensional sectional image (B-mode image) corresponding to the two-dimensional data acquisition area is formed. This image data is sent to an endocardium detecting unit 16.

The endocardium detecting unit 16 is a unit which detects, for example, an endocardium surrounding the left ventricle of the heart on the two-dimensional sectional image. To detect the endocardium, an edge detection technique may for example be used. In this embodiment, after detecting the endocardium, a reference point is manually or automatically set in the middle of the heart cavity (for example, the left ventricle) using a reference point setting unit 18. When the reference point is set, a plural number of (e.g. four) dividing lines radially extending from the reference point are automatically set. Division regions are defined by these dividing lines.

Figure 2:
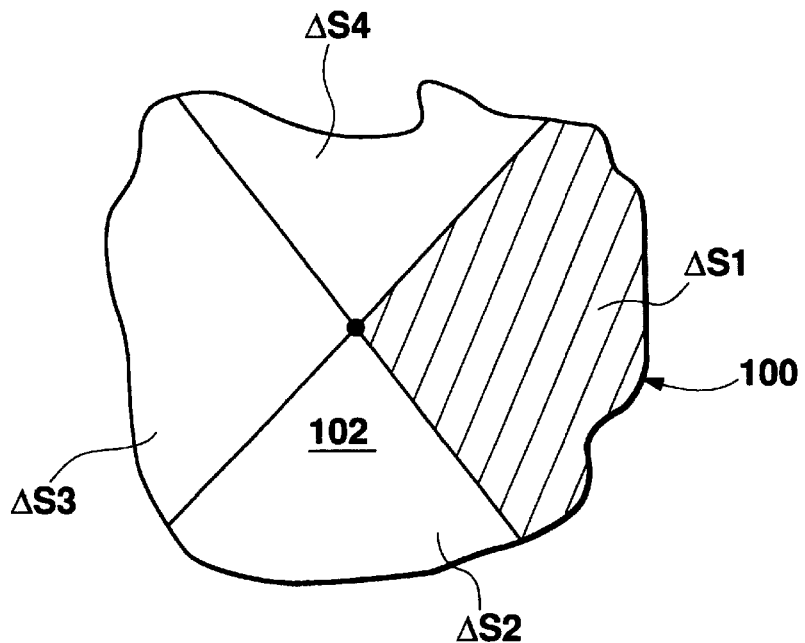
FIG. 2 is a diagram showing the concept of a two-dimensional sectional image comprising the left ventricle. The area inside the left ventricle is divided into four sector-shaped regions.

An outline 100 of the endocardium detected by the above processing and four division regions are shown in FIG. 2. It will be appreciated that edge detection of the outline of the endocardium is not limited to this method and may be performed by various techniques. For example, a large number of reference lines radially extending from the reference point may be set inside the heart cavity, and edge detection performed on each of these reference lines.

A dividing unit 20 shown in FIG. 1 is a means which divides the entire area inside the outline extracted by the endocardium detecting unit 16 into plural sector-shaped regions. The number of division regions may be user-specified by a division number selecting unit 22. In this embodiment, the number of division regions may be arbitrarily selected by the user from 4, 5 and 6. The dividing unit 20 divides the inside of a left ventricle 102 into the set number of division regions as shown in FIG. 2 (in FIG. 2, the interior of the left ventricle is divided into four). In this case, the spreading angles of the division regions may be equal, but for parts where for example there is a likelihood of cardiac infarction, the spreading angle may be adjusted accordingly. Alternatively, the spreading angles of all the division regions can be made different.

An area computing unit 24 shown in FIG. 1 is a means for computing the area of each division region, as shown in FIG. 2. Specifically, the area is computed by, for example, counting the number of pixels in each region divided by the dividing unit 20. Therefore, if electronic scanning by the ultrasonic wave beam is repeated by the probe 10, the area of each division region in each time phase of the heart's motion is output continuously by the area computing unit 24 for each transmitted/received wave frame.

An electrocardiograph 25 is connected to a reference area determining unit 26. The reference area determining unit 26 determines the timing of the end diastolic of the heart based on the R-wave in the electrocardiac signal. The areas of each division region at the time of the end diastolic are taken to be reference areas.

An area variation rate computing unit 28 is a means for computing the ratio of the area of each division region output by the area computing unit 24 to the reference area. Specifically, the following calculations are performed to give an area variation rate FAC.

$$FAC = \{(EDA - \Delta S)/EDA\} \times 100(\%)$$

Figure 3:
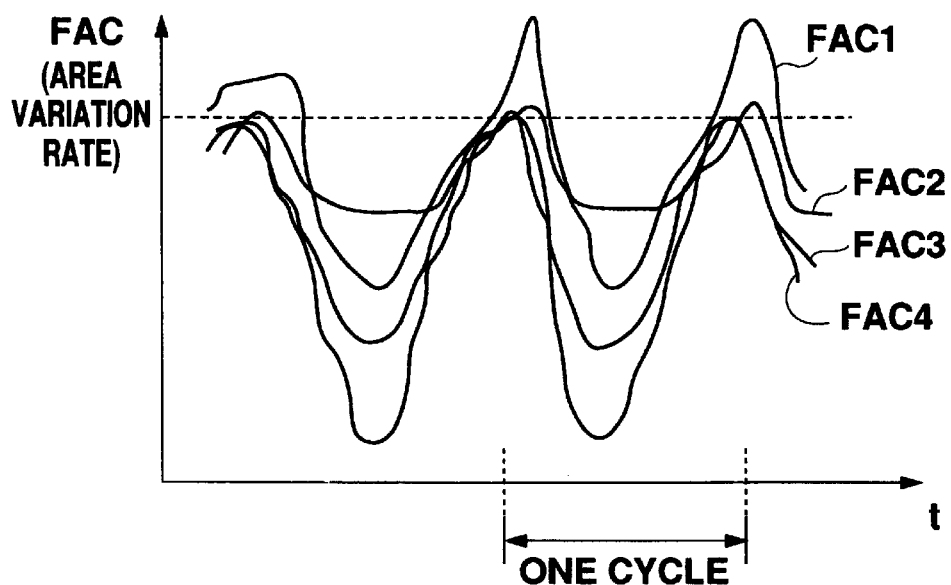
FIG. 3 is a diagram showing an example of a graph relating to this invention representing a variation of an area variation rate of plural division regions.

In the aforesaid equation, EDA represents the area of each division region at the time of the end diastolic (reference area), and $\Delta S$ represents the area of each division region in each time phase. The area variation rate FAC calculated in this way is output by a graph drawing unit 30. The graph drawing unit 30 draws the graph shown in FIG. 3.

Here, the horizontal axis in the graph is the time axis, and the vertical axis represents the FAC of each division region. When the left ventricle is divided into four, for example, as shown in the figure, four curves are shown on the graph. These curves change relative to each other in real time in synchronism with the movement of the heart.

A curve which corresponds to a part where there is a cardiac infarction, for example, is different from the other curves. As a result, the presence or absence of heart disease and the position of heart disease can be diagnosed. If a very large number of such curves is displayed, it is difficult to identify a diseased part, however since according to this embodiment an appropriate number of curves, e.g. four or six, is displayed, a diseased part can be seen at a glance. A display unit 32 of FIG. 1 is a device which displays the graph shown in FIG. 3.

In the embodiment shown in FIG. 1, the electrocardiograph 25 was used, however the aforesaid calculation can be performed using other body signals. Also, although it is preferable to compute the area variation rate by the equation given above, it may be computed by other equations.

What is claimed is:

1. An ultrasonic diagnostic apparatus comprising:

a transmitting/receiving wave unit for sending and receiving ultrasonic waves, and acquiring two-dimensional image data for each transmitted/received wave frame, an extracting unit for extracting an outline of a ventricle or an atrium of a heart based on said two-dimensional image data, a dividing unit for radially dividing an area inside said outline into plural division regions from a reference point set in said ventricle or atrium, an area computing unit for computing an area of each of said division regions for each of said transmitted/received wave frames, and a graph drawing unit for drawing a graph showing a time-dependent variation of the area or an area variation rate of each division region.

2. An ultrasonic diagnostic apparatus as defined in claim 1, wherein said graph includes a horizontal time axis and a vertical axis which is the area or the area variation rate of each division region.

3. An ultrasonic diagnostic apparatus as defined in claim 2, wherein said graph drawing unit is adapted to draw said graph being formed of plural curves, said plural curves representing the area or the area variation rate corresponding to said plural division regions.

4. An ultrasonic diagnostic apparatus as defined in claim 1, wherein said outline includes 4–6 division regions formed inside said outline.

5. An ultrasonic diagnostic apparatus as defined in claim 1, wherein said plural division regions have sizes which are set to be equal to each other.

6. An ultrasonic diagnostic apparatus as defined in claim 1, wherein at least one of said plural division regions has a size different from the other division regions.

7. An ultrasonic diagnostic apparatus as defined in claim 1, wherein the plural division regions have a spreading angle which is variable.

8. An ultrasonic diagnostic apparatus comprising the following:

an electrocardiograph for outputting a diagnostic signal, a transmitting/receiving wave unit for sending and receiving ultrasonic waves, and acquiring two-dimensional image data for each transmitted/received wave frame, an extracting unit for extracting an outline of a ventricle or an atrium of a heart based on said two-dimension image data, a dividing unit for radially dividing an area inside said outline into plural division regions from a reference point set in said ventricle or atrium, an area computing unit for computing an area of each of said division regions for each of said transmitted/received wave frames, and an area variation rate computing unit for computing an area variation rate from the area in each time phase and a reference area for each division region based on said electrocardiograph signal, the reference area being an area of each of said division regions in a predetermined time phase, and a graph drawing unit for drawing a graph showing a time-dependent variation of the area variation rate of each division region.

9. An ultrasonic diagnostic apparatus as defined in claim 8, wherein said area variation rate computing unit performs the following computation for computing the area variation rate:

$$FAC = \{(EDA - \Delta S)/EDA\} \times 100 \ (\%)$$

where FAC is the area variation rate,

EDA is the area in the division region at the end diastolic (reference area), and $\Delta S$ is an area in the division region at a time t.

10. An ultrasonic diagnostic apparatus comprising the following:

a probe for transmitting and receiving ultrasonic waves, an extracting unit for extracting an outline of the cardiac muscle in the heart by using an edge detection method based on two-dimensional image data obtained by transmitting and receiving ultrasonic waves, a dividing unit for dividing the interior of said outline into plural sector-shaped regions, an area computing unit for computing the areas of said plural sector-shaped regions, a graph drawing unit for drawing a graph representing the area variations of said plural sector-shaped regions, and a display unit for displaying said graph.

11. An ultrasonic diagnostic apparatus as defined in claim 10, wherein said drawing unit is adapted to draw said graph being formed of plural curves, said plural curves corresponding to said section-shaped regions.

* * * * *

UNITED STATES PATENT AND TRADEMARK OFFICE
CERTIFICATE OF CORRECTION

PATENT NO.    : 6,135,959
DATED         : October 24, 2000
INVENTOR(S)   : Murashita et al.

It is certified that error appears in the above-identified patent and that said Letters Patent is hereby corrected as shown below:

Title page,
Insert Item:
-- [56]  FOREIGN PATENT DOCUMENTS
9-253085 9/1997 Japan --

Signed and Sealed this

Thirteenth Day of July, 2004

JON W. DUDAS
*Acting Director of the United States Patent and Trademark Office*